United States Patent [19]

Santi

[11] 4,286,565
[45] Sep. 1, 1981

[54] ENGINE CONTROL INSTALLATION

[75] Inventor: Giunio G. Santi, Milan, Italy

[73] Assignee: S.S.O.S. Sub Sea Oil Services S.p.A., Milan, Italy

[21] Appl. No.: 61,992

[22] Filed: Jul. 30, 1979

[30] Foreign Application Priority Data

Aug. 4, 1978 [IT] Italy .................. 26473 A/78
Feb. 9, 1979 [IT] Italy .................. 20060 A/79

[51] Int. Cl.³ .................................... F02M 25/06
[52] U.S. Cl. ............................ 123/568; 123/571; 123/569
[58] Field of Search ........ 123/119 A, 279, 278, 123/568, 569, 570, 571; 60/278, 279

[56] References Cited

U.S. PATENT DOCUMENTS

| 881,803 | 3/1908 | Jaubert | 123/119 A |
|---|---|---|---|
| 883,240 | 3/1908 | Sabathé | 123/119 A |
| 1,099,445 | 6/1914 | Jaubert | 123/119 A |
| 1,750,919 | 3/1930 | Becker | 123/119 A |
| 2,017,481 | 10/1935 | Von Opel | 123/119 A |
| 2,147,671 | 2/1939 | Pratt | 60/279 |
| 2,187,074 | 1/1940 | Caproni | 123/119 A |
| 2,720,856 | 10/1915 | Hoke, Jr. | 123/119 A |
| 2,742,885 | 4/1956 | Thwaites et al. | 123/119 A |
| 2,884,912 | 5/1959 | Lewis | 123/119 A |
| 3,435,810 | 4/1969 | Busse | 60/279 |
| 3,559,402 | 2/1971 | Stone et al. | 123/119 A |
| 3,566,610 | 3/1971 | Fiore | 60/279 |
| 3,775,976 | 12/1973 | Karic | 123/119 A |

Primary Examiner—Wendell E. Burns
Attorney, Agent, or Firm—Darbo & Vandenburgh

[57] ABSTRACT

The exhaust gas of a diesel engine is washed and then a centrifugal separator divides the gas into an $O_2$ enriched component and a $CO_2$ enriched component. Additional oxygen is added to the former component and it is used by the engine for combustion purposes. Water in a pressurized tank is employed to remove $CO_2$ from the $CO_2$ enriched component. Thereafter the latter is fed back to the gas stream going to the engine for combustion.

1 Claim, 1 Drawing Figure

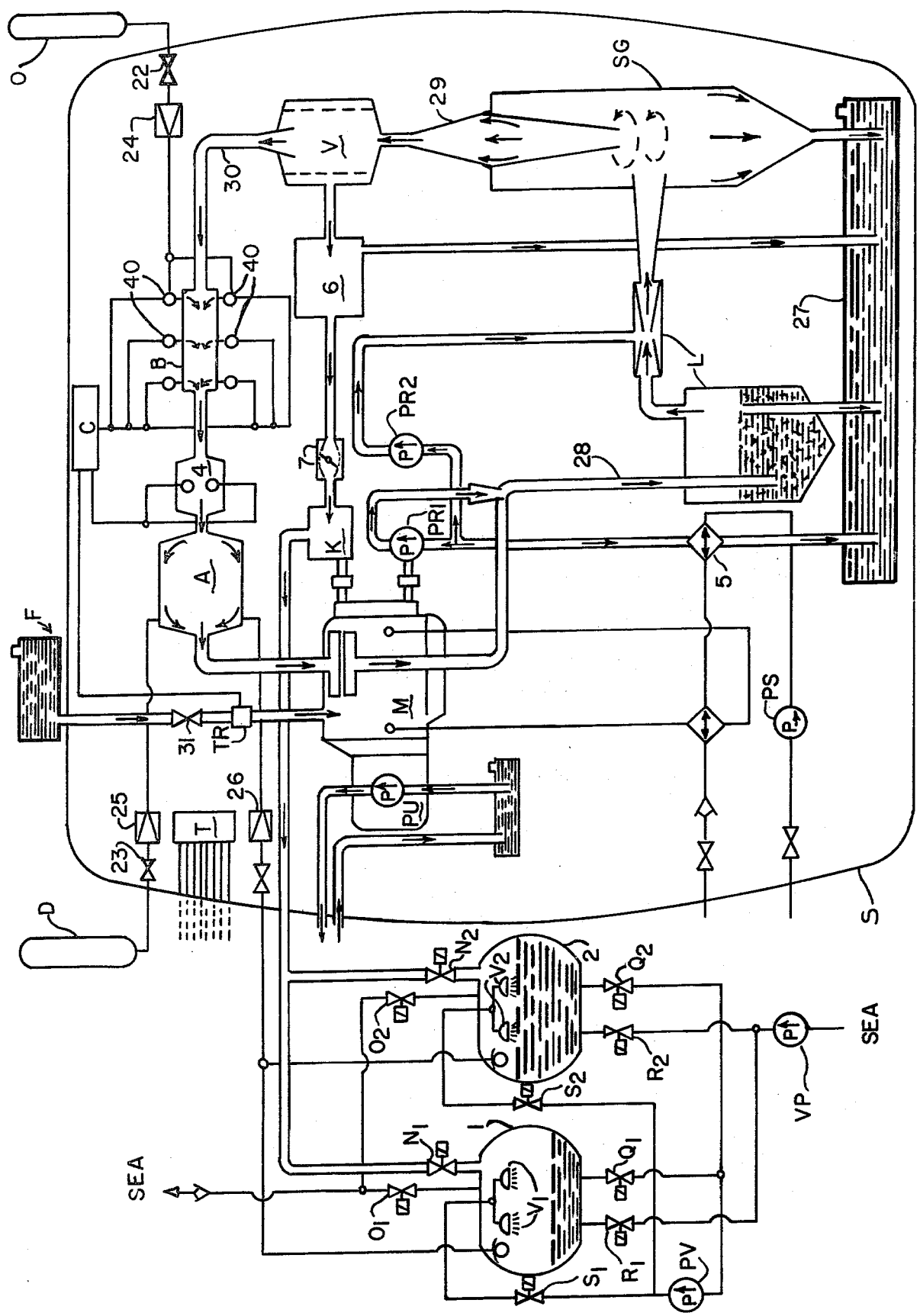

ENGINE CONTROL INSTALLATION

BACKGROUND AND SUMMARY OF THE INVENTION

This invention relates to an engine control installation and more particularly concerns an installation for starting and operating an engine intended for submarine operation or otherwise operating in an environment which lacks air.

A need exists to develop internal combustion engines for submarines which are capable of covering the field of application existing between accumulator operation and atomic operation. This need has been felt for a long time and has even greater significance today due to the applications in the field of research and exploitation of the seabed with the aid of submarines of small displacement and medium power but of the longest possible range.

The results of the studies and trials hitherto performed with a view to the development of an engine which could fulfill this need have not yet led to the realization of a satisfactory serviceable unit.

The basic idea pursued by all researchers was to use a conventional internal combustion engine and to convert the latter, after it had been started, into an internal combustion engine with exhaust gas feedback for submarine operation. This basic idea imposed a serious compromise because the internal combustion engine must be operated in continuous service with a medium, the physical and thermodynamic characteristics of which differ greatly from the characteristics underlying the design of the internal combustion engine. The necessity of starting the engine with air also makes it necessary to carry an appropriate quantity of air for possible underwater starting.

To particularize, the following disadvantages have appeared in these experiments and have certainly negated the possibility of realizing a technically satisfactory engine for submarine operation hitherto:

The unavoidable reduction in the thermodynamic efficiencies and hence the increased consumption of fuel and combustion support; here the increased consumption of combustion support obviously represents the most highly critical condition for the submarine unit.

The necessity to preheat the intake mixture so that adequate temperature values can be attained after compression; the preheating of the gas mixture, as it has been performed in isolated cases by mixing the gases fed back after the scavenging with a part of the exhaust gases, also involves contamination problems in the internal combustion engine.

The necessity to carry on board an appropriate supply of compressed air for possible underwater starting.

An object of the present invention is to obviate these and other disadvantages. The invention is based upon an underlying idea which is totally different from the prior art, that the internal combustion engine should, from the starting process, embrace those peculiar operating conditions which are determined by submarine operation. In this way it becomes possible to develop an internal combustion engine which is capable of providing optimum performance even in an environment of other than air, so that one escapes the compromise which was imposed by the conventional double use, namely, starting with air and continuous operation with a medium other than air.

According to the present invention I provide an installation for starting and operating an engine intended for operation in an environment lacking air, characterized by an internal combustion engine so designed that it is operated with a gas mixture of previously prepared composition both during starting, and in continuous operation, while the previously prepared composition is chosen with a view to the optimum operating capacity which can be attained by the internal combustion engine.

An internal combustion engine based on the diesel principle has been taken as a basis for study. The unit has successfully passed the capability tests and can be considered as a serviceable unit.

The following principles were taken into consideration in the application of the idea of the invention with a view to achieving optimum results:

Choice of the gas mixture and of the type of fuel with a view to optimum conditions for efficiency and consumption, also practical possibilities for a simple and economical reproduction of the optimum intake mixture during continuous operation.

The problems related to accident safety also had to be taken into consideration, particularly since—since it is a question of dosing the gas mixture with pure oxygen—the possibilities of the use of gas mixtures enriched with oxygen may be considered with a view to improving efficiency.

Use of such measuring, control and supply devices for fuel and oxygen as permit the optimum conditions for the combustion process and the stability of the internal combustion engine.

Choice of the mechanical characteristics of the internal combustion engine which lead to optimum performance with the chosen gas mixture. The study of this problem revealed that an internal combustion engine for exclusive submarine operation, in which the efficiency values are required to be optimized, must be designed almost entirely "ad hoc". The most important differences compared to an engine for submarine operation which has been designed according to the previous principles of other researchers, are to be seen principally in the compresion ratio, the geometry of the combustion chamber, the stroke ratio, the preinjection and the injection time.

Use of devices which permit such a separation of the carbon dioxide produced as a combustion product from the exhaust gas, so that the carbon dioxide can be removed and the oxygen still present in the exhaust gas can be recovered in a more or less complete manner.

Use of devices for a simple and economic removal of the combustion products (essentially carbon dioxide and steam) from the circuit of the internal combustion engine, more particularly with the property of not being constrained to the immersion depth of the installation.

The gas mixture of previously prepared composition conveniently consists essentially of combustion gases, a fuel gas (e.g., $O_2$) and optionally further inert gases.

In a preferred embodiment the installation according to the invention incorporates at least one tank in which the gas mixture of a previously prepared composition is contained.

In a preferred embodiment the installation includes a device for monitoring and regulating the oxygen supply necessary for submarine operation, which comprises means for measuring the instantaneous oil delivery rate, means for measuring the instantaneous percentage oxygen content in the intake mixture of the internal combustion engine, while said percentage oxygen content can be deduced from the function "sound transmission velocity in gas mixture-temperature", and an electronic calculator which serves to evaluate the two measured values detected with the aid of the above means, to compare them with prescribed optimum values for the operation of the internal combustion engine and, as dictated by that comparison, to control an oxygen dosing device for the oxygen supply to the intake mixture.

The said means of measuring the instantaneous percentage oxygen content in the intake mixture of the internal combustion engine are based upon the knowledge that the sound transmission velocity in a continuous gaseous medium is a function of the characteristics of the gas and of the temperature in accordance with the known relation:

$$V = \sqrt{\gamma RT}$$

wherein
V = sound transmission velocity in the gas mixture,
$\gamma$ = ratio $c_p/c_v$ of the specific heat at constant pressure to the specific heat at constant volume of the gas mixture,
R = characteristic constant of the gas mixture,
T = absolute temperature of the gas mixture.

The measurement of the temperature of the gas mixture (carbon dioxide, oxygen and steam) makes it possible to reduce the number of unknowns in the composition of the gas mixture from 3 ($CO_2$, $O_2$, $H_2O$) to 2 ($CO_2$, $O_2$). It is therefore possible to deduce from the measurement of the sound trasmission velocity at a given temperature, the value of the parameter $\gamma R$ which is a function of the percentage content of the constituents $CO_2$ and $O_2$ which constitute the gas mixture.

The dosing device for the oxygen supply to the intake mixture is conveniently controlled by electric valves which control a continuous oxygen current of variable quantity which is produced as the sum of discrete partial oxygen currents.

In a preferred embodiment the installation includes a device for recovering the oxygen present in the exhaust gas, which comprises means for the centrifugal separation of the carbon dioxide utilizing the different inertias and viscosities of the two gases.

In a preferred embodiment the installation includes a device for removing the combustion products from the circuit of the internal combustion engine and for recovering the residual oxygen, which comprises a low pressure enclosed compressor, means for the automatic monitoring of the gas delivery rate of the compressor with a sensor to detect variations in the gas pressure in the circuit, a water pump system and treatment tank(s) for gas-sea water treatment with minimum energy consumption constant at all immersion depths, and with automatic monitoring of the weights of the treated media.

Means to separate the water by condensation and store the separated water on board may be provided in the device for removing the combustion products in manner known per se.

In a preferred embodiment, the compressor belonging to the device to remove the combustion products is provided according to the invention with a throttle flap arranged in the intake pipe, which permits a regulation of the delivery rate of the compressor in the sense that the pressure in the circuit of the internal combustion engine exhibits a constant value.

To control the throttle flap, a pneumatic and/or electric-electronic control device influenced by the absolute pressure in the circuit is preferably provided.

DESCRIPTION OF THE DRAWING

The drawing shows, in simplified form, a diagram of an installation according to the invention as applied to a diesel engine for submarine operation.

DESCRIPTION OF SPECIFIC EMBODIMENT

The following disclosure is offered for public dissemination in return for the grant of a patent. Although it is detailed to ensure adequacy and aid understanding, this is not intended to prejudice that purpose of a patent which is to cover each new inventive concept therein no matter how others may later disguise it by variations in form or additions or further improvements.

The installation comprises the following components:
a pressureproof tank S in which the entire installation is contained, except for the system for treating and removing the surplus gases, and the fuel and combustion support tanks, but these latter parts could also optionally be located inside the pressureproof tank S;
an internal combustion engine (diesel engine) M;
a power generator PU driven by the engine;
a system L for washing and cooling the exhaust gases;
a system for fresh water circulation in a circuit for washing and cooling the exhaust gases, comprising a header tank 27, a fresh water/sea water heat exchanger 5, pumps PR1, PR2 to circulate and spray the washing water, a pump PS for sea water circulation and a swirl generator and cyclone SG;
a centrifugal separator V for $O_2$ recovery and for separating the surplus $CO_2$, which communicates with the swirl generator and cyclone through a pipeline 29;
a system B for oxygen dosing, which is connected to the system V through a pipeline 30 and is provided with electric valves 23 for injecting $O_2$ through nozzles into the gaseous medium circuit of the internal combustion engine;
a system A for mixing the intake gas for the engine;
an ultrasonic gas analyzer 4 for the intake gas;
a flow meter TR to measure the instantaneous engine fuel delivery rate;
a calculator C to control the valves 40 of the oxygen dosing device B;
a fuel tank F;
a high pressure tank D which contains a gas mixture of previously prepared composition and is equipped with a shut-off valve 23 and a relief valve 25 in the gas conduit to the system A;
a high pressure tank system O which serves for oxygen storage and is equipped with a shut-off valve 22 and a relief valve 24 in the $O_2$ conduit leading to the valves 40;
a system for removing $CO_2$ from the circuit of the internal combustion engine, comprising a storage chamber 6, a control valve in the form of a throttle flap 7, an enclosed compressor K, one or more tank sets each set comprising two tanks (1, 2) (of which only one tank set is shown in the drawing), which serve for receiving the gases, for treating them with sea water and for clearing the used treatment water overboard, a pressure relief valve 26 for optional recovery of the oxygen present in the exhaust gas, electric valves $N_1$, $N_2$, $O_1$, $O_2$, $Q_1$, $Q_2$, $R_1$, $R_2$, $S_1$ and $S_2$, pumps PV, VP and atomizers $V_1$ and $V_2$, while the said work cycles are performed consecutively as dictated by the commands of a water level and pressure monitoring device T.

PRINCIPLE OF OPERATION OF THE INSTALLATION

Starting

For the initial start and for further starting after repairs or after work in the surface state which permit an access of air into the circuit of the internal combustion engine, the following procedure is used:

(a) After closing valves 31 and 22 and manually opening valves $O_1$, $O_2$, $N_1$, $N_2$, switching off the monitoring device T and opening the valve 23, the internal combustion engine M is set in rotation by means of its starter motor so that the air which has penetrated is expelled from the circuit of the internal combustion engine and replaced by a gas mixture of $CO_2$ and $O_2$ or pure $CO_2$ from tank D.

(b) After completing step (a) the valves 23, $O_1$, $O_2$, $N_1$, $N_2$, are closed, the monitoring device T is switched on again and the valves 31 and 22 are opened.

After checking that no more nitrogen is contained in the circuit, the internal combustion engine can now be started.

For starting in the submerged state the procedure commences with step (b), because no nitrogen can be contained in the circuit.

Continuous Operation

The exhaust gases enriched with steam and $CO_2$ originating from the combustion process are pumped through the pipeline 28 into the washing system L.

Here an appropriate quantity of water taken from the tank 27 is injected and sprayed by the pump system PR1, PR2 which cools the exhaust gases by condensation of the excess steam contained therein and also collects the solid particles and unburnt substances present in the exhaust gases. The system L contains a swirl generator and cyclone SG, which separate liquids and solids out of the gases. These liquids and solids are collected at the circumference and fed to the tank 27. On the other hand, the purified gases carried through the pipe 29 pass into the centrifugal separator V.

In the latter unit, due to the different specific gravity of $CO_2$ compared to oxygen, a separation occurs such that the peripheral layers become enriched with $CO_2$ and the central layers with $O_2$. The gases already enriched with $O_2$ pass through the central pipe 30 to the dosing device B, where they are further enriched with the additional quantity of oxygen which is required in order to attain the percentage necessary for a satisfactory combustion process.

The gases from the dosing device then pass through the gas analyzer 4 into the mixer A and from there to the intake pipe of the internal combustion engine M. The calculator C receives at its input the data on the instantaneous fuel consumption, which are determined continuously by the flow meter TR in the fuel supply line, and also the instantaneous value of the percentage $O_2$ content in the gases flowing through the mixer A, which is determined by means of the gas analyzer 4. By processing the data fed in in real time the calculator delivers at its output the information for the control of the (at least four) electric valves 40 of the dosing device B. These electric valves have finely adjusted nozzles, the flow rates of which correspond to values increasing in geometric progression.

The combination of these flow rates makes possible a precise dosing of the oxygen supplied.

The gases enriched with $CO_2$ at the circumference of the centrifugal separator V pass automatically into the storage chamber 6, where the liquid residues therein are collected and returned into the tank 27.

The gases are sucked out of the storage chamber 6 through the throttle flap 7 by the enclosed compressor K and pumped at low pressure into the system 1, 2 (or systems) for gas treatment and for removal of the used treatment water.

The throttle flap 7 is controlled by a pneumatic and/or electric-electronic control device which reacts to the absolute pressure in the circuit of the internal combustion engine so that the delivery rate of the enclosed compressor K is regulated in the sense of maintaining this pressure constant.

The gas treatment and used treatment water removal system is arranged so that in the course of each work cycle, under appropriate control by the relevant electric valves, one at a time of the tanks belonging to each tank set serves to receive the compressed gases and the other tank for the treatment of water saturated with $CO_2$ and topping up with clean water.

For a better understanding of the principle of operation of this system, a work cycle, e.g., the work cycle in which the tank 2 is charged with gas coming from the compressor K, will now be described in detail. At the beginning of this work cycle the tank 2 is full of clean water and the tank 1 is full of gas compressed to the maximum pressure of the compressor.

The work cycle commences when the electric valves N, O, Q, R, S assume the following positions under the control of the monitoring device T:

| Open valves | Closed Valves |
|---|---|
| $N_2$ | $N_1$ |
|  | $O_1, O_2$ |
| $Q_2$ | $Q_1$ |
|  | $R_1, R_2$ |
| $S_1$ | $S_2$ |

In this state, while the compressor is supplying the tank 2 with gas, the pump PV sucks the water out of the tank 2 and pumps it to the spray heads $V_1$ where it is atomized into the tank 1.

With rising water level in the tank 1 the pressure rises and the $CO_2$ is absorbed in constantly increasing quantity by the water. When the adjusted pressure value (e.g., 50 atmospheres) of the relief valve 26 is attained this valve opens and allows the gases, now enriched in $O_2$, which are present in the top part of the tank 1, to flow into the circuit of the internal combustion engine so that the residual content of $O_2$, if any, still contained in the gases to be expelled is recovered.

When valve 26 opens to feed $O_2$ rich gas to the circuit of the internal combustion engine, the tank 1 fills with water. A float valve (only indicated in the drawing) in tank 1 supplies a signal to the monitoring device T and that device closes valves $S_1$, $Q_2$ and opens valves $R_1$, $O_1$. Thus the washing phase of the tank 1 commences, which is performed by the pump VP using sea water. This work phase is completed when the predetermined (low) pressure value in the tank 2 (e.g., 8 atmospheres) is attained.

The work cycle just described is now repeated with mutual exchange of the functions of the two tanks 1 and 2.

With this system, because the response pressure of the relief valve 26 is fixed, the powers to drive the compressor K and to drive the pumps PV and VP at uniform load of the internal combustion engine are desirably constant values independent of the immersion depth.

The gas analyzer 4 is disclosed in greter detail, and claimed, in my application entitled GAS ANALYZER filed concurrently herewith, and the disclosure of that application is incorporated herein by reference.

I claim:

1. An internal combustion engine installation wherein said engine has an intake for receiving an oxidizible fuel and a gas intake for receiving an oxidizing fuel gas and an exhaust at which the products of combustion, including carbon dioxide gas, are discharged along with some unburned oxidizing fuel gas, said installation including
   closed circuit conduit means interconnecting said exhaust and said gas intake for receiving said gases at said exhaust and for feeding back a portion of said received gases to said gas intake, said conduit means including centrifugal separator means for dividing said received gases into two partial streams, one of which has a higher concentration of $O_2$ than did the received gases and the other of which has a higher concentration of $CO_2$ than did the received gases, said conduit means delivering said one partial stream to said gas intake.

2. An installation as set forth in claim 1 including carbon dioxide removal means connected to said conduit means to receive said other partial stream, remove a significant amount of the $CO_2$ therefrom and then return the remainder of said other partial stream to the conduit means for delivery to the engine gas intake, said carbon dioxide removal means comprising:
   a treatment tank, a low pressure compressor for connecting said conduit means and said tank feeding said other partial stream to said treatment tank, and water treatment means connected to said tank for intimately contacting the gases in said tank with water and for increasing the fluid pressure in the tank whereby the water in the tank will take up a significant amount of the $CO_2$ present in the gases in the tank.

3. An installation as set forth in claim 2, wherein said carbon dioxide removal means includes
   another treatment tank, and valve and conduit means connecting the two treatment tanks in parallel for use alternately for receiving said other partial stream and the removal of a significant amount of $CO_2$ therefrom.

4. An installation as set forth in claim 3, wherein said water and treatment means pumps water from a first of the tanks cut off from said compressor into the second of the tanks which is receiving said other partial stream from said compressor and when said significant amount of $CO_2$ has been removed from the gases in the second of the tanks the water therein is expelled by additional fresh water which additional fresh water is then used for addition to the first of the tanks during the alternate part of the cycle during which the first of the tanks is receiving said other partial stream.

5. An installation as set forth in claim 4, wherein said carbon dioxide removal means includes, upstream of said compressor, a control valve for regulating the delivery rate of the compressor in the sense that the pressure of said portion of said gases in said conduit means remains constant.

6. An installation as set forth in claim 4, including control means connected to the valve and conduit means for cycling the function of the two treatment tanks and including sensors in each tank respectively responsive to a relatively high water level in the tanks respectively.

7. An installation as set forth in claim 2,
   wherein said conduit means includes gas scrubber means for cleaning said exhaust gases and removing the water therefrom, said gas scrubber means including a water collection tank; and
   including a tank forming a storage chamber between said centrifugal separator means and said control valve, means connecting said storage chamber and said gas scrubber means for returning liquid from said storage chamber to said water collection tank.

8. An installation as set forth in claim 1, wherein said conduit means includes gas scrubber means for cleaning said exhaust gases and removing the water therefrom, said gas scrubber means being upstream of said centrifugal separator means and including in series means for contacting said exhaust gases with water and a swirl generator and cyclone.

* * * * *